(12) United States Patent
Fenton et al.

(10) Patent No.: US 7,758,614 B2
(45) Date of Patent: Jul. 20, 2010

(54) COUPLING MEMBER FOR KNOTLESS SUTURES AND LIGATURES

(75) Inventors: Paul V. Fenton, Marblehead, MA (US); Paul A. Westhaver, Newburyport, MA (US)

(73) Assignee: Tornier, Inc., Edina, MN (US)

( * ) Notice: Subject to any disclaimer, the term of this patent is extended or adjusted under 35 U.S.C. 154(b) by 0 days.

(21) Appl. No.: 10/117,576

(22) Filed: Apr. 5, 2002

(65) Prior Publication Data

US 2002/0173821 A1 Nov. 21, 2002

Related U.S. Application Data

(63) Continuation-in-part of application No. 09/607,880, filed on Jun. 30, 2000, now Pat. No. 6,423,088, which is a continuation-in-part of application No. 09/349,663, filed on Jul. 8, 1999, now Pat. No. 6,409,743.

(60) Provisional application No. 60/092,072, filed on Jul. 8, 1998, provisional application No. 60/092,074, filed on Jul. 8, 1998.

(51) Int. Cl.
*A61B 17/04* (2006.01)
(52) U.S. Cl. ..................... 606/232; 156/73.2
(58) Field of Classification Search ................ 606/232, 606/228, 233, 151, 148, 300, 74; 228/136; 156/73.1, 73.2; 292/256.61; 24/130, 129 W, 24/456, 703.1, 703.2
See application file for complete search history.

(56) References Cited

U.S. PATENT DOCUMENTS

| | | | |
|---|---|---|---|
| 1,822,330 A | 9/1931 | Ainslie | |
| 2,336,689 A | 12/1943 | Karle | |
| 2,461,030 A * | 2/1949 | Brickman | ................ 228/136 |
| 3,113,408 A | 12/1963 | Kirkpatrick et al. | |
| 3,407,777 A | 10/1968 | Anastasio et al. | |
| 3,462,803 A | 8/1969 | Horton | |
| 3,503,119 A | 3/1970 | Seitz, Jr. et al. | |
| 3,513,848 A | 5/1970 | Winston et al. | |
| 3,516,631 A | 6/1970 | Santucci | |
| 3,608,539 A | 9/1971 | Miller | |
| 3,664,345 A | 5/1972 | Dabbs et al. | |
| 3,802,438 A | 4/1974 | Wolvek | |
| 3,857,396 A | 12/1974 | Hardwick | |
| 3,879,981 A | 4/1975 | Richards | |
| 3,995,870 A | 12/1976 | Hulek | |
| 4,050,100 A | 9/1977 | Barry | |
| 4,265,246 A | 5/1981 | Barry | |
| 4,291,698 A | 9/1981 | Fuchs et al. | |
| 4,312,337 A | 1/1982 | Donohue | |
| 4,369,787 A | 1/1983 | Lasner et al. | |
| 4,561,153 A | 12/1985 | Matsui | |
| 4,583,540 A | 4/1986 | Malmin | |

(Continued)

*Primary Examiner*—Eduardo C Robert
*Assistant Examiner*—David Comstock
(74) *Attorney, Agent, or Firm*—Faegre & Benson LLP

(57) ABSTRACT

A knotless suture device including at least one fusible suture for securing or ligating living tissue structures. The device also includes a generally U-shape fusible coupling member for receiving end portions of the fusible suture. Energy applied to fusible portions of the coupling member cause localized heating and plastic flow so as to fuse the coupling member and the end portion of the suture together. The coupling member can include one or more energy directors on a contact surface to direct and focus energy to particular regions so as to efficiently effect coupling member-to-suture welding.

8 Claims, 3 Drawing Sheets

U.S. PATENT DOCUMENTS

| | | |
|---|---|---|
| 4,588,408 A | 5/1986 | Yamada |
| 4,590,929 A | 5/1986 | Klein |
| 4,635,638 A | 1/1987 | Weintraub |
| 4,896,668 A * | 1/1990 | Popoff et al. .................. 606/74 |
| 4,930,502 A | 6/1990 | Chen |
| 4,935,027 A | 6/1990 | Yoon |
| 4,957,498 A | 9/1990 | Caspari et al. |
| 5,078,731 A | 1/1992 | Hayhurst |
| 5,356,417 A | 10/1994 | Golds |
| 5,376,101 A | 12/1994 | Green et al. |
| 5,383,883 A | 1/1995 | Wilk et al. |
| 5,383,905 A | 1/1995 | Golds et al. |
| 5,391,173 A | 2/1995 | Wilk |
| 5,413,585 A | 5/1995 | Pagedas |
| 5,417,700 A | 5/1995 | Egan |
| 5,425,489 A | 6/1995 | Shichman et al. |
| 5,437,685 A | 8/1995 | Blasnik |
| 5,500,018 A | 3/1996 | Spotorno et al. |
| 5,527,341 A | 6/1996 | Gogolewski et al. |
| 5,586,983 A | 12/1996 | Sanders et al. |
| 5,593,425 A | 1/1997 | Bonutti et al. |
| 5,611,801 A * | 3/1997 | Songer ........................ 606/73 |
| 5,618,311 A | 4/1997 | Gryskiewicz |
| 5,643,289 A | 7/1997 | Sauer et al. |
| 5,732,530 A | 3/1998 | Pfaff |
| 5,735,877 A | 4/1998 | Pagedas |
| 5,766,218 A | 6/1998 | Arnott |
| 5,769,894 A | 6/1998 | Ferragamo |
| 5,881,452 A | 3/1999 | Nowell, III et al. |
| 5,893,880 A | 4/1999 | Egan et al. |
| 5,941,901 A | 8/1999 | Egan |
| 6,047,708 A * | 4/2000 | Panel et al. .................. 132/273 |
| 6,174,324 B1 * | 1/2001 | Egan et al. .................. 606/232 |

* cited by examiner

COUPLING MEMBER FOR KNOTLESS SUTURES AND LIGATURES

CROSS REFERENCE TO RELATED APPLICATIONS

This application is a continuation in part of U.S. application Ser. No. 09/607,880, filed Jun. 30, 2000, (now U.S. Pat. No. 6,423,088 issued Jul. 7, 2002) which is a continuation in part of U.S. application Ser. No. 09/349,663, filed Jul. 8, 1999, (now U.S. Pat. No. 6,409,743 issued Jun. 6, 2002) which claims priority to provisional U.S. patent application Ser. Nos. 60/092,072 and 60/092,074, both filed Jul. 8, 1998. Each of these four applications are hereby incorporated by reference into this application.

FIELD OF THE INVENTION

The present invention relates generally to devices and methods for securing a suture(s) without knots, and for securing living tissue structures together without knotted sutures.

BACKGROUND OF THE INVENTION

In minimally invasive surgical procedures that use elongated instruments and videoscopic viewing of the surgery site, there is significant difficulty in knot tying and wound approximating. Traditional methods of wound closure routinely involve the use of individual hand-knotted sutures. The suture strands are directed through portions of tissue to be joined and formed into a single stitch, which is then knotted. However, due to the location of the area being sutured, the delicate nature of anatomical features, and the stiffness of the suture used, it can be difficult to tie uniform stitches to close the wound that do not unravel or tie off (or ligate) a vessel. Non-uniform stitches (i.e., stitches of varying tension) or varied bite size (depth into the tissue) can cause uneven healing, localized trauma, infection, and patient discomfort.

To reduce the discomfort and aid healing, it is desirable to secure sutures uniformly and close to a wound. Due to the stiffness of some sutures, knotting the sutures can be difficult, particularly when the tissue to be sutured is deep within the body. Typical knots may be relatively large and elevated above the tissue being sutured, which can increase patient discomfort.

It is also desirable in many surgical procedures where sutures are used, to reduce the size of, or eliminate, the knot bundle associated with a knotted suture and to minimize the amount of foreign material in the body. The knot bundle can become an irritant and retard the healing process and cause discomfort or pain for the patient. The knot bundle can also be a source of infection.

Methods known in the art to overcome these problems include various suture securing devices such as buttons, and methods of fusing synthetic sutures. Although buttons can produce sutures with even tension and without the concomitant dexterity of knot tying, their elevated location above the wound or within the body cavity can cause irritation and discomfort. Furthermore, there is a risk of button migration, since they are discrete objects in the body.

Suture fusion techniques, whereby synthetic polymer suture strands are melted together by the application of heat or other energy to the sutures, are known in the art. Examples of devices to perform such suture fusion are disclosed in U.S. Pat. No. 5,417,700, assigned to the assignee of this application and incorporated herein by reference. However, some polymeric sutures are not amenable to this process. For example, braided or multi-filament sutures may not completely fuse since spaces between the individual strands may interfere with the heat or energy transfer needed for fusion to occur. As a result, the sutures may be incompletely fused, and the resulting joint may fail.

It would be advantageous to provide suture and tissue joining devices which are fusible to and/or around sutures and other structures, including living tissue, so as to avoid the need for suture knots.

SUMMARY OF THE INVENTION

According to one aspect of the invention, there is provided a closed suture loop formed from one or more elongated members or the same elongated member looped upon itself. The closed suture loop includes a fusible open or U-shaped coupling member that is disposed about an open interior region which extends about a central axis. A fusible inner surface of the coupling member defines the open interior region.

In one embodiment, the elongated members are surgical sutures which are made of a fusible material. End portions of the sutures are adapted to fuse to each other and also to the interior surface of the coupling member in a knotless weld upon application of sufficient energy to the end portions and the coupling member.

In another embodiment, the sutures are made of non-fusible, or minimally fusible material and only the interior surface of the coupling member is fusible so that upon an application of energy, the sutures are depressed into softened portions of the interior surface. In another embodiment, the sutures are made of braided material that is marginally fusible. In another embodiment, the elongated member comprises a band of material that encircles a bundle of other structures, such as blood vessels, for example, for ligation.

The coupling member is preferably made of a thermoplastic polymeric material. The elongated members can be surgical sutures which are also made of a fusible, thermoplastic polymeric material. In another embodiment, the elongated members can be living tissue structures. The energy for fusing the members may be generated from a variety of sources known in the art, such as for example, thermal energy, optical energy, radio-frequency energy, current sources or more preferably, ultrasonic energy.

In another exemplary embodiment, the open or U-shaped coupling member includes one or more energy directors extending from an interior surface. The energy directors define fusion regions for the sutures and the coupling member and are adapted to focus applied energy to the fusion regions so that the sutures and coupling member fuse together preferentially at the fusion regions.

The inside surface of the coupling member may also be smooth, or have protrusions, grooves or other texturing to aid in securing the partially encircled structures.

According to another aspect of the present invention, there is provided a kit for forming knotless sutures or ligatures. The kit includes a fusible open or U-shaped coupling member as described above, and a fusing tool which positions the coupling member around end portions of the elongated member positioned in the interior region. The fusing tool applies energy to the end portions and the coupling member so that those end portions and the coupling member are mutually joined by fusion. The fusing tool includes generally an energy source, a welding head, an end effector, and general electronics, switches, control devices and the like for supplying weld energy and activating the end effector.

In one exemplary embodiment of the fusing tool, the energy source is ultrasonic energy, and the fusing tool includes an ultrasonic transducer, an ultrasonic welding horn, and an end effector. The end effector may include one or more jaw members adapted for selective deployment around at least a portion of the coupling member to form an ultrasonic welding anvil. In various embodiments, the end effector can be a pair of opposable jaws which move with respect to each other, or a pair of jaws which are resiliently biased toward each other.

In additional exemplary embodiments, energy for bonding is supplied by thermal energy (e.g., heat), optical energy (e.g., laser generated), electrical energy (e.g., radio frequency, RF), or current sources (e.g., resistive heating).

According to another aspect of the present invention, there is provided a kit for joining a plurality of surgical sutures together without a knot. The kit provides a fusible coupling member as described above and a fusing tool as described above. The fusing tool is for biasing end portions of sutures toward the interior surface of the coupling member, and applying fusion energy so that the suture end portions are securely retained to the coupling member.

BRIEF DESCRIPTION OF THE DRAWINGS

For a fuller understanding of the nature and objects of the present invention, reference should be made to the following detailed description taken in connection with the accompanying drawings, in which.

Like features in the figures are labeled with like reference characters.

DESCRIPTION OF THE PREFERRED EMBODIMENTS

Figure 1:
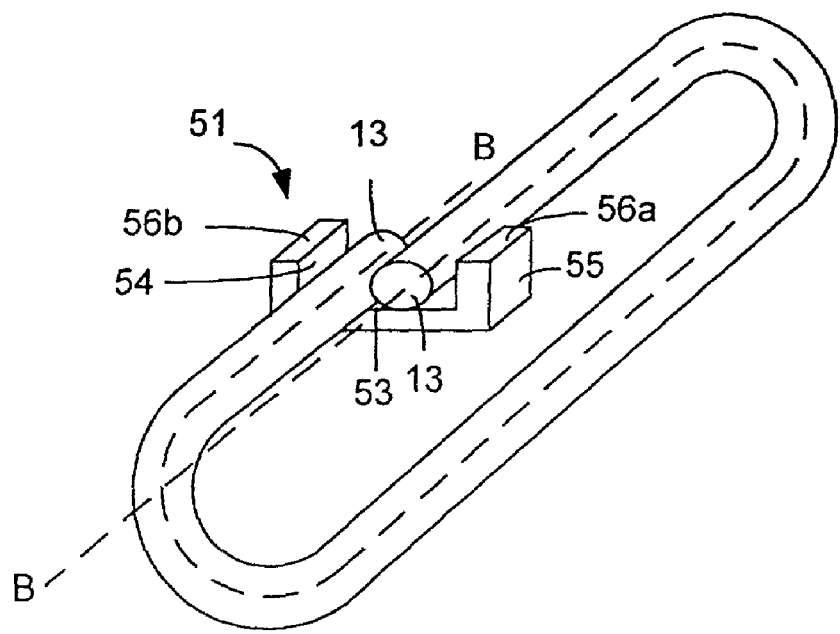
FIG. 1 is an oblique view of an exemplary embodiment of a coupling member constructed in accordance with the present invention fused to end portions of an elongated member in the form of a suture.
Figure 2:
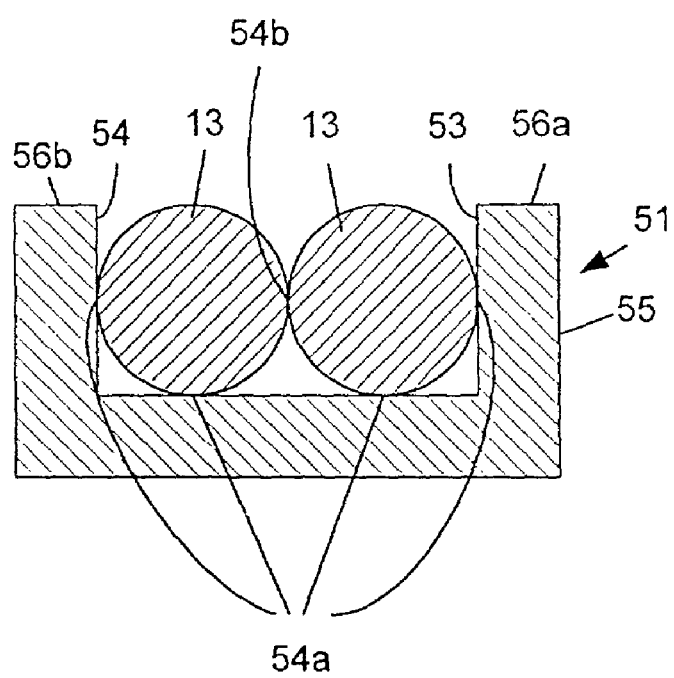
FIG. 2 is cross-sectional view of the coupling member and the end portions of the suture of FIG. 1.

FIGS. 1 and 2 show an exemplary embodiment of a substantially U-shape coupling member 51 retaining end portions 13 of a flexible fusible elongated member 14 extending along a curved axis B-B. The flexible fusible elongated member can comprise a suture 14 (for suturing). The flexible fusible elongated member can also comprise more than one suture and/or living tissue structure (for ligation). The U-shape coupling member 51 defines an open interior region 53 between two end portions 56a and 56b thereof. The coupling member also has an interior surface 54 and an exterior surface 55 extending between the two end portions 56a and 56b.

FIGS. 1 and 2 show the coupling member 51 and the end portions 13 of the suture 14 fused. Preferably the end portions 13 are pressed against each other, and toward the interior surface 54, to the point of deformation, thereby increasing their mutual contact surface areas.

Depending on the selection of materials for the coupling member 51 and the suture 14, fusion can occur in selected regions, i.e., interface regions 54a between the coupling member 51 and the suture 14, and at interface regions 54b between the end portions 13 of the suture 14. The coupling member 51 is preferably made of a biocompatible material which in some forms of the invention, is sufficiently flexible to allow for moderate deformation of the coupling member 51 to allow the suture 14 (or anatomical structures) to be securely placed within the interior region 53. In one form, the material is resilient so as to retain the structures within the coupling member 51 and create contact surfaces for fused interface regions. Any type of material that meets these requirements can be used.

The coupling member 51 material is also capable of being fused or joined to the suture 14 material upon the application of energy, such as thermal energy (heat), optical energy (laser generated), electrical energy (radio frequency, RF), current sources (resistive heating), or preferably ultrasonic energy, to the coupling member. Preferred materials are synthetic polymers capable of being repeatedly softened or melted with the application of heat or pressure (commonly known as thermoplastics). Thermosetting plastics and other heat-fusible materials may also be suitable for use as a coupling member 51 under certain conditions. The coupling member 51 can be made by methods known in the art, such as, but not limited to, machining, injection molding, extrusion, thermoforming and the like.

If desired, the coupling member 51 can be made of a first material and the suture made of a second material having a melting temperature different from the first material, so as to further direct the melting and fusing upon the application of energy to the coupling member 51. Higher melting point materials may be preferred for the coupling member 51, particularly if a braided or multi-filament suture 14 is used, as the bonding energy can fuse underlying fibers as well as the suture itself. The energy required to melt the material using the various processes and the time required for the molten material to resolidify are well known in the art.

The suture 14 can be of any type customarily used for surgery, such as silk, but preferred materials are polymers such as PTFE, and especially preferred material are thermoplastics, such as polyamide (nylon), polypropylene, polyester, polyglycolic acid (PGA), polyglyconate, and polydioxanone. The suture 14 can be either substantially monofilamentous, multiple stranded, twisted, braided, or otherwise interlinked material. Filament of the suture 14 can have any cross-sectional shape, such as substantially circular, elliptical or rectangular.

The choice of materials for the suture 14 and the coupling member 51, and the geometry of the coupling member 51 and the suture determines where fusing occurs. For example, if the coupling member 51 and the suture 14 are made from materials with largely differing melting temperatures (e.g., if the coupling member 51 is a thermoset polymer and the suture is a thermoplastic polymer), the bonds occur at the suture to suture interface 54b (and within the individual fibers that make up the suture in the case of a multi filament or braided suture), but little or no fusing occurs at the interface 54a between the suture 14 and the coupling member 51. Conversely, when the coupling member 51 is made of a thermoplastic material and the suture 14 is made of a thermoset polymer, or when an anatomical feature is within the coupling member 51, fusing of the coupling member 51 to itself occurs at any overlap areas. This could be beneficial for retaining ligaments, vessels or ducts, while allowing the coupling member 51 to move relative to the ligaments, vessels or ducts retained therein, or for ligating a vessel or duct. In a most preferred embodiment, however, the coupling member 51 and the suture 14 are both made of a material(s) that melts at about the same temperature (e.g., both are made of thermoplastic polymers). Using the same material allows for bonds to occur at all or any of the contact interfaces 54a, 54b described above.

Figure 2A:
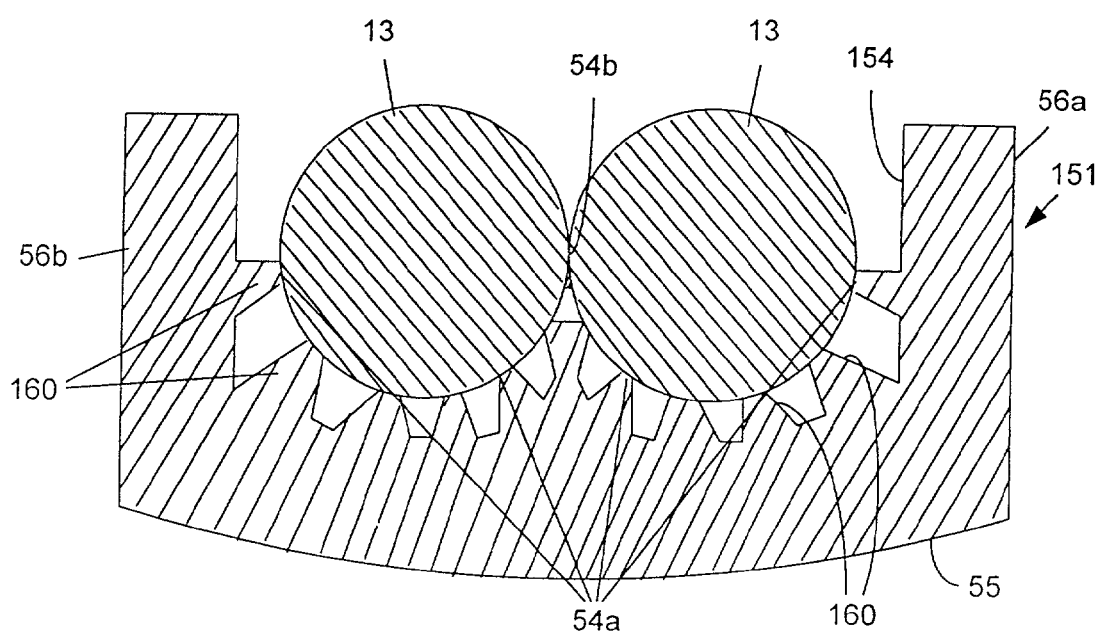
FIG. 2A is cross-sectional view of another exemplary embodiment of a coupling member constructed in accordance with the present invention shown holding end portions of a suture.

The interior region 53 of the U-shaped coupling member 51 is large enough to permit the end portions 13 of the suture 14 (or tissue structures) to be secured therein. As shown in FIGS. 1 and 2, the interior surface 54 of the coupling member 51 can be smooth. FIG. 2A, however, shows another exemplary embodiment of a coupling member 151 of the present invention, having an interior surface 154 that is grooved and has protrusions 160. The interior surface 54 of the coupling member 51 of the present invention can also be textured in other ways to create a roughened surface area to enhance contact between the coupling member 51 and structures therein. The roughened surface area is particularly useful when securing a coupling member 51 to a piece if living tissue such as a ligament.

Figure 4:
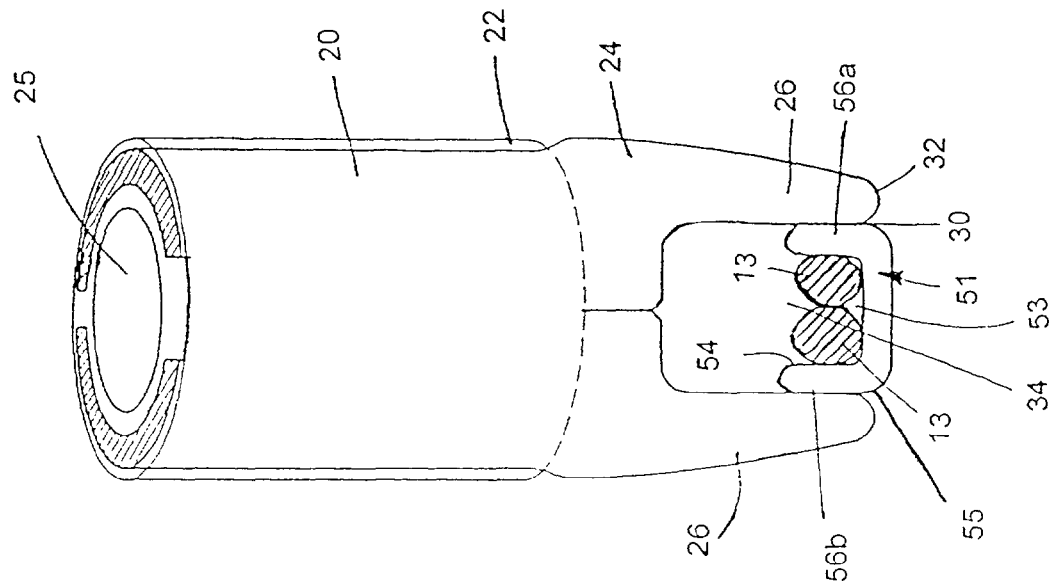
FIG. 4 is an oblique view of an end effector of the fusing tool of FIG. 3 positioned around the coupling member and the end portions of the suture prior to being fused together.
Figure 3:
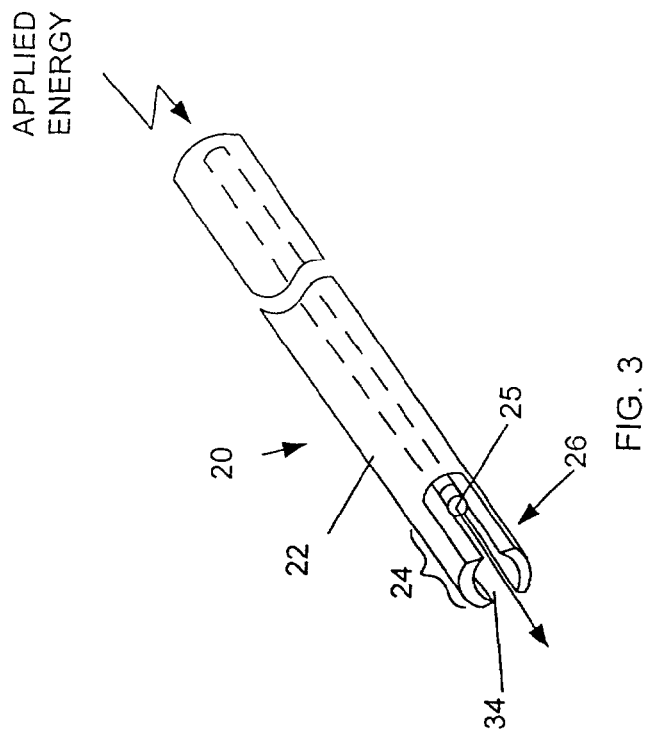
FIG. 3 is an oblique view of a fusing tool for use with the coupling member of FIG. 1.

An exemplary embodiment of a fusing tool 30 constructed in accordance with the present invention is shown in FIG. 3. The tool 20 is used to compress and fuse the coupling member 51 and the end portions 13 of the suture, as shown in FIG. 4. The fusing tool 20 includes a delivery shaft 22, a welding horn 25, and an end effector 24 adapted to cradle and compress the coupling member 51 around the suture 14. The welding horn 25 is mounted at a distal end of the delivery shaft 22, and surrounded by the end effector 24, which is formed from a plurality of resiliently mounted rigid prongs 26 extending from the shaft 22. The prongs 26 can expand slightly to accept the coupling member 51, and then contract to hold the coupling member 51 securely and apply moderate compression to the coupling member 51 and the suture 14 within the coupling member.

The fusing tool 20 and the coupling member 51 or a plurality of the coupling members 51 can be provided as a kit. The kit may also include various end effectors 24 that are interchangeable on the tool shaft 22 for accommodating different coupling member 51 shapes and sizes.

Referring to FIGS. 3 and 4, the prongs 26 define an aperture 34 for holding the coupling member 51 during positioning, compression and fusing of the coupling member 51 and the suture 14 therein. The prongs 26 are spaced apart by sufficient distance to allow the coupling member 51 to fit snugly yet releasably therebetween. An interior surface 30 of the prongs 26 can be smooth, grooved or otherwise textured to enhance contact between the coupling member 51 and the prongs 26.

In addition, flattened or rounded ends 32 on the prongs 26 allow for the tip to abut living tissue when the end portions 13 of the suture 14 are pulled tight through the coupling member 51, such as at a wound site, thereby minimizing any gaps in the tissue to be joined and maintaining a desired tension on the suture 14. In one embodiment, the prongs 26 can also function as an anvil. In other embodiments, underlying bone, tissue, anatomical features, or other materials temporarily or permanently placed under the effector 25 may also act as an anvil. The latter design may be preferable if it is necessary or otherwise advantageous to secure the coupling member 51 as closely as possible to tissue so as to permit minimal gapping between the joined suture 14 and the coupling member 51.

The disclosure may be embodied in other specific forms without departing from the spirit or essential characteristics thereof. The present embodiments are therefore to be considered in all respects as illustrative and not restrictive, the scope of the disclosure being indicated by the appended claims rather than by the foregoing description. All changes that come within the meaning and range of the equivalency of the claims are therefore intended to be embraced therein

What is claimed is:

1. A closed suture loop, comprising:
a U-shaped coupling member extending along a central axis between a first coupler end and a second coupler end, said U-shaped coupling member having a fusible interior surface including a plurality of energy directors and an exterior surface extending between said first coupler end and said second coupler end, and defining an open interior region bounded by said interior surface, each of the plurality of energy directors extending from said interior surface to a distal tip in the interior region, said distal tip being spaced apart from said interior surface, wherein a groove formed in the interior surface between at least two of the plurality of energy directors is narrower than the open interior region;

a flexible fusible elongated member extending along a curved axis between a first portion at a first suture end and a second portion at a second suture end, wherein said first portion and said second portion are mutually adjacent and oppositely directed, said first portion and said second portion being disposed in said interior region with said suture axis of said first portion and said second portion being substantially parallel with said central axis;

wherein the elongated member comprises a surgical suture material, wherein said first portion of the suture is fused to said second portion and said first portion and said second portion are fused to said interior surface of said coupling member, the plurality of energy directors defining fusion regions of the sutures and the coupling member and being adapted to focus energy applied to the coupling member to the fusion regions so that one or more of the elongated members and coupling member are fusible together at the fusion regions.

2. The closed suture loop according to claim 1, wherein the elongated member comprises a band of material adapted for securing a plurality of anatomical structures together.

3. The closed suture loop according to claim 1, wherein the plurality of energy directors includes one or more protrusions extending from said interior surface into said interior region and adapted to secure the elongated members within the central region.

4. The closed suture loop according to claim 3, wherein the protrusions are tapered.

5. The closed suture loop according to claim 1, wherein the elongated members comprise living tissue structures.

6. The closed suture loop according to claim 1, wherein the energy applied to the coupling member is ultrasonic energy.

7. The closed suture loop according to claim 1, wherein the energy applied to the coupling member is selected from the group consisting of thermal energy, optical energy, electrical energy and current sources.

8. The closed suture loop according to claim 1, wherein the coupling member is made of a thermoplastic polymeric material.

* * * * *